| (12) | United States Patent | (10) Patent No.: US 12,268,764 B2 |
|---|---|---|
| | Stebbins et al. | (45) Date of Patent: Apr. 8, 2025 |

(54) COLOR- AND CLARITY-STABLE NATURAL MICELLAR WATER

(71) Applicant: L'OREAL, Paris (FR)

(72) Inventors: Nicholas David Stebbins, Clark, NJ (US); Susan Halpern Chirch, Basking Ridge, NJ (US); Ryuji Hara, Westfield, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/668,580

(22) Filed: Oct. 30, 2019

(65) Prior Publication Data

US 2021/0128420 A1    May 6, 2021

(51) Int. Cl.
| *A61K 8/02* | (2006.01) |
| *A61K 8/34* | (2006.01) |
| *A61K 8/36* | (2006.01) |
| *A61K 8/368* | (2006.01) |
| *A61K 8/42* | (2006.01) |
| *A61K 8/44* | (2006.01) |
| *A61K 8/60* | (2006.01) |
| *A61Q 1/14* | (2006.01) |
| *A61Q 5/02* | (2006.01) |
| *A61Q 19/10* | (2006.01) |

(52) U.S. Cl.
CPC .............. *A61K 8/0291* (2013.01); *A61K 8/34* (2013.01); *A61K 8/345* (2013.01); *A61K 8/36* (2013.01); *A61K 8/368* (2013.01); *A61K 8/42* (2013.01); *A61K 8/44* (2013.01); *A61K 8/442* (2013.01); *A61K 8/604* (2013.01); *A61Q 1/14* (2013.01); *A61Q 19/10* (2013.01); *A61K 2800/28* (2013.01); *A61K 2800/524* (2013.01); *A61K 2800/592* (2013.01); *A61K 2800/596* (2013.01); *A61Q 5/02* (2013.01)

(58) Field of Classification Search
None
See application file for complete search history.

(56) References Cited

U.S. PATENT DOCUMENTS

| 5,928,993 A | 7/1999 | Johansson et al. | |
| 2010/0215598 A1* | 8/2010 | Poletti | A61Q 1/14 |
| | | | 424/59 |
| 2014/0349902 A1* | 11/2014 | Allef | A61Q 19/10 |
| | | | 510/491 |
| 2015/0064128 A1* | 3/2015 | Matsubara | A61K 8/731 |
| | | | 424/70.13 |
| 2015/0239993 A1* | 8/2015 | Miyoshi | A61Q 5/065 |
| | | | 424/70.13 |
| 2018/0098923 A1* | 4/2018 | Hutton, III | A61K 8/42 |
| 2019/0142706 A1* | 5/2019 | Sverdlove | A61Q 19/007 |
| | | | 514/788 |
| 2020/0010598 A1* | 1/2020 | Fischer | C08F 2/14 |
| 2021/0196604 A1* | 7/2021 | Rowney | A61K 8/463 |

FOREIGN PATENT DOCUMENTS

WO    WO 1996034078    10/1996

OTHER PUBLICATIONS

Potassium sorbate (from Sciencemadness Wiki)—an internet article obtained at the website: http://www.sciencemadness.org/smwiki/index.php/Potassium_sorbate#:~:text=Potassium%20sorbate%20is%20easily%20produced%20by%20neutralizing%20sorbic%20acid%20with%20potassium%20hydroxide. (Year: 2018).*
"Garnier SkinActive Water Rose Micellar Cleansing Water" (a product advertisement by Target (dated Oct. 23, 2019) taken from the website: https://www.target.com/p/garnier-skinactive-water-rose-micellar-cleansing-water-13-5-fl-oz/-/A-76545862) (Year: 2019).*
"SkinActive Micellar Cleansing Water & Makeup Remover w/ Rose Water, For Normal to Dry Skin, 23.7 fl oz" (an ad by Walgreens (Sep. 18, 2019) from the website: https://www.walgreens.com/store/c/skinactive-micellar-cleansing-water-&-makeup-remover-w/-rose-water,-for-normal-to-dry-skin/ID=300396097-product ). (Year: 2019).*
"Garnier SkinActive Micellar Cleansing Water Now Contains Rose Water and Other Rosy Skincare Offerings for Fall" (online product review article by Musings of a Muse (Sep. 9, 2019) obtained from: https://www.musingsofamuse.com/2019/09/garnier-skinactive-micellar-cleansing-water-with-rose-water.html) (Year: 2019).*

* cited by examiner

*Primary Examiner* — Sin J Lee
(74) *Attorney, Agent, or Firm* — Laetitia Leproust; Rob Klemz

(57) ABSTRACT

The present disclosure relates to an aqueous micellar liquid composition that include an amphoteric surfactant, an alkyl glucoside and a specific preservative system. In particular, the compositions include: a) an amphoteric surfactant; b) an alkyl glucoside and c) sodium benzoate. The compositions are low foaming upon rubbing and stable.

13 Claims, No Drawings

COLOR- AND CLARITY-STABLE NATURAL MICELLAR WATER

FIELD OF THE DISCLOSURE

The present disclosure relates to micellar liquid compositions that includes a combination of amphoteric surfactant, alkyl glucoside and sodium benzoate in order to obtain a color and clarity stable natural micellar water with high makeup removability.

BACKGROUND

Surfactants are widely used in aqueous based personal care, household, and industrial products. They are typically used as wetting agents, detergents, and emulsifiers. In personal care cleansing products (e.g., shampoos, body washes, facial cleansers, liquid hand soaps, etc.) the surfactant is often the most important component because it provides many of the cleansing attributes of the composition.

Aqueous based cleansers such as micellar water have become very popular with consumers. It is desirable for such skin cleansers to clean the skin easily.

There is a need of aqueous based cleansers which are low foaming but still exhibiting very good cleaning properties and very good makeup removability as well as a very good stability. This is challenging but have been achieved in the instant case.

SUMMARY OF THE DISCLOSURE

The present disclosure relates to aqueous micellar liquid compositions that include:
a) From about 0.2% to about 1.2% of an amphoteric surfactant by weight based on the total weight of the composition,
b) From about 0.06% to about 0.9% of an alkyl polyglucoside by weight based on the total weight of the composition,
c) From about at least 0.05% of a preservative system, the said preservative system is sodium benzoate, by weight based on the total weight of the composition, and
Wherein the preservative system stabilizes the aqueous micellar liquid composition.

In one or more embodiments, the sodium benzoate stabilizes the aqueous micellar liquid composition. In some embodiments, the presence of sodium benzoate prevents the composition to become yellow.

In some embodiments, the sodium benzoate is present in the amount from about up to 0.5% by weight based on the total weight of the composition.

In one or more embodiments, the amphoteric surfactant is selected from the group consisted of coco-betaine, lauryl betaine, oxyethylenated, lauryl betaine, oxyethylenated stearyl betaine, cocamidopropyl betaine, lauramidopropyl betaine and mixtures thereof. In one embodiment, the amphoteric surfactant is coco-betaine. In some embodiments, the amphoteric surfactant is from about 0.3% to about 1% by weight based on the total weight of the composition.

In one or more embodiments, the alkyl polysaccharide is selected from alkyl polyglucoside, polyglycerol esters, alkylpolyglucosides, alkyl(ether)phosphates, fatty acid alkanolamides, and a mixture thereof. In some embodiments, the alkyl polyglucoside is selected from the group consisting of lauryl glucoside, octyl glucoside, decyl glucoside, coco glucoside, sucrose laurate, caprylyl/capryl glucoside, and sodium lauryl glucose carboxylate and a mixture thereof. In one embodiment, the alkyl polyglucoside is caprylyl/capryl glucoside. In some embodiments, the alkyl glucoside is from about 0.1% to about 0.5% by weight based on the total weight of the composition.

In some embodiments, the aqueous micellar liquid compositions may further comprise one or more water-soluble solvents selected from the groups consisting of glycerin, C1-4 alcohols, organic solvents, polyols, glycols, and a mixture thereof. In one or more embodiments, the one or more water-soluble solvents is propanediol.

Another aspect of the instant disclosure can include an aqueous micellar liquid composition comprising:
a) From about 0.2% to about 1.2% of coco-betaine by weight based on the total weight of the composition,
b) From about 0.06% to about 0.9% of caprylyl/capryl glucoside by weight based on the total weight of the composition,
c) From about 0.01% to about 0.5% of sodium benzoate by weight based on the total weight of the composition,
d) A water-soluble solvent.

The aqueous micellar liquid compositions are useful for treating the skin, in particular the skin of the face. The compositions can be used as a facial wash, makeup remover, and/or a moisturizer, as the products are particularly effective at cleansing, hydrating, and strengthening the skin.

Another aspect of the instant disclosure can include a method for removing makeup from keratinous fibers. The methods comprise applying the aqueous micellar liquid compositions to the keratinous fibers to the skin upon which makeup is applied, and removing at least a portion of the makeup from the keratinous fibers.

Some aspects of the instant disclosure can include a method for cleansing the skin comprising applying the aqueous micellar liquid compositions to the skin and removing at least a portion of the composition from the skin The methods generally include applying the aqueous micellar composition to the skin. For example, the hands and/or a cotton ball or pad (or other device, for example, a cloth, a tissue, a wipe, etc.) may be used to apply the mixture to the skin. A cotton ball or pad (or other device) can also be used to absorb and remove dirt, grease, unwanted makeup, etc. from the skin.

The aqueous micellar liquid composition of the instant disclosure provides unexpected stability with a very good make up removal thanks to the presence of a particular preservative, in this case sodium benzoate.

DETAILED DESCRIPTION OF THE DISCLOSURE

The instant disclosure relates to compositions for cleansing the skin.

The aqueous micellar liquid compositions of the instant disclosure, in the broadest sense, typically include the following:
a) From about 0.2% to about 1.2% of an amphoteric surfactant by weight based on the total weight of the composition,
b) From about 0.06% to about 0.9% of an alkyl polyglucoside by weight based on the total weight of the composition,
c) From about at least 0.05% of a preservative system, said preservative system is sodium benzoate, by weight based on the total weight of the composition.

The aqueous micellar liquid compositions of the instant disclosure exhibit a surprisingly stable preservative system unique to the micellar liquid composition.

As used herein, the term "micellar liquid composition" means that it is a type of microemulsion.

A "micelle" is an aggregate or supramolecular assembly of surfactant molecules dispersed in a liquid (an aqueous phase in the instant case). Micellar systems are a special class of dispersions or microemulsions that are typically transparent or translucent.

Amphoteric (Zwitterionic) Surfactant

Non-limiting examples of amphoteric surfactants include, in addition to betaines, sultaines, amphoacetates, and amphoprionates.

In some embodiments, the amphoteric surfactant of (a), may be, for example a compound selected from the group consisted of betaines, coco-betaine, (C8-C20)alkyl betaines, (C8-C20)alkylamido(C1-C6)alkylbetaines, lauryl betaine, oxyethylenated, lauryl betaine, oxyethylenated stearyl betaine, cocamidopropyl betaine, lauramidopropyl betaine and mixtures thereof.

Mention may in particular be made, as betaines, of (C8-C20)alkyl betaines, such as, for example, coco betaine, such as the product sold under the name Dehyton AB-30® by the company Cognis, lauryl betaine, such as the product sold under the name Genagen KB® by the company Clariant, oxyethylenated (10 EO) lauryl betaine, such as the product sold under the name Lauryl Ether (10 EO) Betaine® by the company Shin Nihon Rica, or oxyethylenated (10 EO) stearyl betaine, such as the product sold under the name Stearyl Ether (10 EO) Betaine® by the company Shin Nihon Rica.

Mention may be made, among (C8-C20)alkylamido(C1-C6)alkylbetaines and derivatives thereof, for example, of cocamidopropyl betaine, sold under the name Lebon 2000 HG® by the company Sanyo or sold under the name Empigen BB® by the company Albright & Wilson, or lauramidopropyl betaine, sold under the name Rewoteric AMB12P® by the company Witco.

In some embodiments, betaines and amphoprionates can be used, and most typically betaines. Betaines which can be used in the current compositions include those having the formulas (XXIIA-D) below:

(XXII A-B)

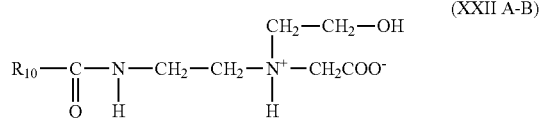

(XXII C)

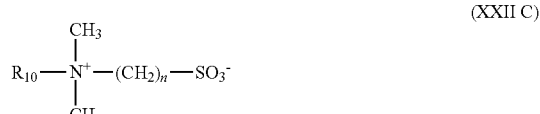

(XXII D)

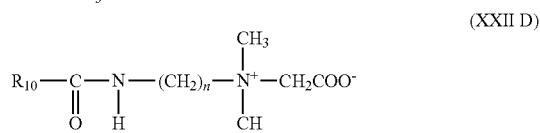

Wherein $R^{10}$ is an alkyl group having 8-18 carbon atoms; and n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically coco betaine.

Hydroxyl sultaines useful in the compositions of the present disclosure include the following

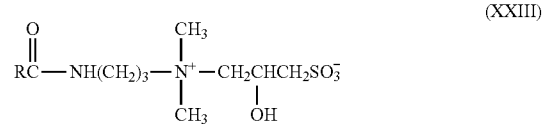

(XXIII)

wherein

R is an alkyl group having 8-18 carbon atoms.

Useful alkylamphoacetates include those having the formula (XXIV)

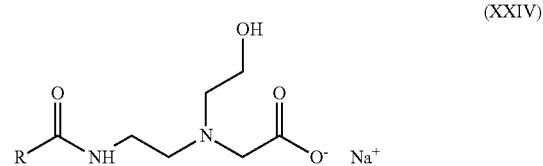

(XXIV)

wherein

R is an alkyl group having 8-18 carbon atoms.

useful alkyl amphodiacetates include those having the formula (XXV)

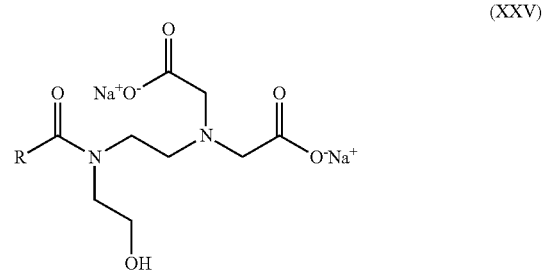

(XXV)

Wherein

R is an alkyl group having 8-18 carbon atoms.

Examples of the amphoteric propionate surfactants that are suitable for the instant disclosure include sodium lauroyl methylaminopropionate, sodium cocaminopropionate, sodium cocaminodipropionate, ammonium cocaminopropionate, ammonium cocaminodipropionate, sodium cocamphopropionate, ammonium cocamphopropionate, triethanonlamine cocamphopropionate, sodium cornamphopropionate, ammonium cornamphopropionate, triehtanonlamine cornamphopropionate, sodium lauraminopropionate, ammonium lauraminopropionate, triethanonlamine lauraminopropionate, sodium lauroamphopropionate, ammonium lauroamphopropionate, triethanonlamine lauroamphopropionate, ammonium lauriminodipropionate, triethanonlamine lauriminodipropionate, disodium lauriminodipropionate, triethanonlamine cocaminopropionate, triethanonlamine cocaminodipropionate, disodium caproamphopropionate, discodium capryloamphodipropionate, disodium cocamphodipropionate, or discodium oleoamphodipropionate.

The amphoteric surfactant may be present in an amount from about 0.2%, 0.25%, 0.3%, 0.35%, 0.4%, 0.45%, 0.5%, 0.55% to about 0.55%, 0.6%, 0.65%, 0.7%, 0.75%, 0.8%, 0.85% to about 0.8%, 0.85%, 0.9%, 0.95%, 1.0%, 1.1%, or 1.2% by weight based on the total weight of the composition. In some embodiments, the amphoteric surfactant is coco-betaine.

Nonionic Surfactant Alkyl Glucoside

In some embodiments, the nonionic surfactant of (b), may be, for example, a compound selected from alkyl polyglucoside, polyglycerol esters, alkyl(ether)phosphates, fatty acid alkanolamides, and a mixture thereof.

Non-limiting examples of nonionic surfactants include polyglycerol esters, alkylpolyglucosides, alkyl(ether)phosphates, fatty acid alkanolamides, and a mixture thereof. Furthermore, in some cases, one or more of the nonionic surfactants has an HLB (hydrophile-lipophile balance) of at least 12, at least 13, or at least 14 to 20. Furthermore, one or more of the nonionic surfactants may have an HLB (hydrophilic-lipophilic balance) of at least 12 to 20, at least 13 to 20, at least 14 to 20, or at least 15 to 20.

The amphiphilic character of small-size surfactants can be characterized by the HLB. The HLB concept is the best-known method to select a surfactant suitable for an application. This semi empirical method assigns a surfactant a HLB number according to its chemical structure. Several experimental and numeric methods have been developed over the years to determine HLB numbers. These methods, initially developed for nonionic surfactants, are mainly based on the respective sizes of the hydrophobic and hydrophilic moieties of the surfactant molecules.

Many nonionic surfactants are known and may be useful. Non-limiting classes of nonionic surfactants include esters of polyols with fatty acids and alkoxylated derivatives thereof, alkylpolyglucosides, sucrose esters, alkoxylated ethers of fatty acids and glucose or alkylglucose, esters of fatty acids and glucose or alkylglucose, sorbitol esters of fatty acids and alkoxylated derivatives thereof, alkoxylated fatty alcohols (for example, ethoxylated fatty alcohols), alkanolamides, polyglylcerol esters, and a mixture thereof. In some cases, one or more nonionic surfactants may be selected from the group consisting of polyglycerol esters, alkylpolyglucosides, alkyl(ether)phosphates, fatty acid alkanolamides, and a mixture thereof. Additionally, one or more polyglycerol esters and/or one or more alkylpolyglucosides may be particularly useful. For example, the product may include polyglyceryl-4 captrate and decyl gucoside.

Alkyl polyglucosides that may be used include compounds of the following formula:

wherein,
R1 is an alkyl group having 8-18 carbon atoms;
R2 is an ethylene or propylene group;
Z is a saccharide group with 5 to 6 carbon atoms;
n is an integer from 0 to 10; and
x is an integer from 1 to 5.

Such alkyl polyglucoside compounds include lauryl glucoside, octyl glucoside, decyl glucoside, coco glucoside, sucrose laurate, caprylyl/capryl glucoside, and sodium lauryl glucose carboxylate, and mixtures thereof. In some cases, at least one alkyl poly glucoside compound is selected from the group consisting of lauryl glucoside, octyl glucoside, decyl glucoside, coco glucoside, sucrose laurate, caprylyl/capryl glucoside, and sodium lauryl glucose carboxylate and a mixture thereof.

Non-limiting examples of alkyl(ether)phosphates include, alkoxylated alkyl phosphate esters and alkyl phosphate esters corresponding to a mono-ester of the following formula and/or a salt thereof:

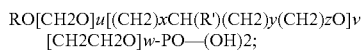

a di-ester corresponding to the following formula and/or a salt thereof:

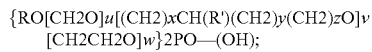

a tri-ester of the following formula and/or a salt thereof:

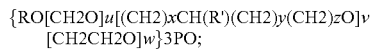

and combinations thereof, wherein:
R is a hydrocarbon radical containing from 6 to 40 carbon atoms;
u, v and w, independently of one another, represent numbers of from 0 to 60;
x, y and z, independently of one another, represent numbers of from 0 to 13;
R' represents hydrogen, alkyl, the sum of x+y+z being ?0. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

Furthermore, in the above three formula, R may be linear or branched, acyclic or cyclic, saturated or unsaturated, aliphatic or aromatic, substituted or unsubstituted, preferably a linear or branched, acyclic C6-40 alkyl or alkenyl group or a C1-40 alkyl phenyl group, more particularly a C8-22 alkyl or alkenyl group or a C4-18 alkyl phenyl group, more preferably a C12-18 alkyl group or alkenyl group or a C6-16 alkyl phenyl group; u, v, w, independently of one another, is preferably a number from 2 to 20, more preferably a number from 3 to 17 and most preferably a number from 5 to 15;

x, y, z, independently of one another, are preferably a number from 2 to 13, more preferably a number from 1 to 10 and most preferably a number from 0 to 8.

More specific, non-limiting examples of alkyl(ether)phosphates include PPG-5-ceteth-10 phosphate, oleth-3 phosphate, oleth-10 phosphate, ceteth-10 phosphate, dicetyl phosphate, cetyl phosphate, and stearyl phosphate.

Non-limiting examples of fatty alkanolamides (fatty acid alkanolamides) t include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.

A more exhaustive list of nonionic surfactants that may be included in the hair-treatment compositions is provided later, under the heading "Nonionic Surfactants."

The nonionic surfactant may be present in an amount from about 0.06%, 0.07%, 0.08%, 0.09%, 0.1%, 0.15%, 0.2%, 0.25%, 0.3%, 0.35%, to about 0.35%, 0.4%, 0.45%, 0.5%, 0.55%, 0.6%, 0.65%, 0.7%, 0.75%, 0.8%, 0.85%, or 0.9% by weight based on the total weight of the composition. In some embodiments, the alkyl polyglucoside is caprylyl/capryl glucoside.

Sodium Benzoate

The total amount of sodium benzoate in the aqueous micellar liquid compositions can vary but is typically from about at least 0.05% and up to about 1% based on the total weight of the aqueous micellar liquid composition.

In some cases, the total amount of sodium benzoate in the aqueous micellar liquid compositions may be from about 0.05%, 0.06%, 0.07%, 0.08%, 0.09%, 0.1%, 0.12%, 0.14%, 0.16%, 0.18%, 0.2%, to about 0.2%, 0.25%, 0.3%, 0.35%, 0.45%, or 0.5% based on the total weight of the aqueous micellar liquid composition.

Water Soluble Solvent

The aqueous micellar liquid composition may further comprise water-soluble solvents. Non-limiting examples of water-soluble solvents include glycerin, C1-4 alcohols, organic solvents, polyols, glycols, and a mixture thereof. In some embodiments, the one or more water-soluble solvents is propanediol.

The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvent has a solubility of at least 60%, 70%, 80%, or 90%. Non-limiting examples of water-soluble solvents include, for example, glycerin, C1-4 alcohols, organic solvents, fatty alcohols, fatty ethers, fatty esters, polyols, glycols, and a mixture thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, diglycerin, erythritol, pentaerythitol, arabitol, adonitol, sorbitol, dulcitol, maltitol, panthenol, xylitol, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some instances, the one or more water-soluble solvents are selected from the group consisting of glycerin, C1-4 alcohols, organic solvents, polyols, glycols, and a mixture thereof.

The aqueous micellar liquid compositions are useful for treating the skin, in particular the skin of the face. The products can be used as a facial wash, makeup remover, and/or a moisturizer, as the products are particularly effective at cleansing, hydrating, and strengthening the skin. Accordingly, the instant disclosure relates to methods for cleansing the skin, methods for hydrating the skin, methods for removing makeup from the skin, methods of strengthening the barrier properties of the skin, etc. The methods generally include applying the composition to the skin. For example, the hands and/or a cotton ball or pad (or other device, for example, a cloth, a tissue, a wipe, etc.) may be used to apply the composition to the skin. A cotton ball or pad (or other device) can also be used to absorb and remove dirt, grease, unwanted makeup, etc. from the skin.

In one embodiment, the instant disclosure relates to a method for cleansing the skin comprising applying the aqueous micellar liquid composition to the skin and removing at least a portion of the product from the skin. In another embodiment, the instant disclosure relates to a method for hydrating the skin comprising applying the aqueous micellar liquid composition to the skin and removing at least a portion of the product from the skin. In another embodiment, the instant disclosure relates to a method for removing makeup from the skin comprising applying the aqueous micellar liquid composition to skin upon which makeup has been applied and removing at least a portion of the makeup from the skin.

Implementation of the present disclosure is provided by way of the following examples. The examples serve to illustrate the technology without being limiting in nature.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "at least one" means one or more and thus includes individual components as well as mixtures/combinations.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

Example 1

Micellar Water Composition

The following Examples are provided for illustrative purposes only, and are not intended to be limiting.

TABLE 1

Inventive Example 1

| COMPONENT | US INCI NAME | AMOUNT (WT. %) |
|---|---|---|
| Surfactant | COCO-BETAINE | 0.45 |
| Surfactant | CAPRYLYL/CAPRYL GLUCOSIDE | 0.3 |
| Preservative | SODIUM BENZOATE | 0.1 |
| Solvent | PROPANEDIOL | 5 |
| pH adjuster | CITRIC ACID | 0.12 |
| Water | WATER | Q.S. |

The Inventive Example was prepared according to the procedure as follows: all the ingredients were mixed in one pot and stirred until completely mixed.

The Inventive Example is an aqueous micellar liquid composition. The composition was shown to be stable and clear when compared with similar compositions containing other preservatives than sodium benzoate. The results are shown in the next section.

Example 2

Stability Experiments

Stability experiments were conducted to show the importance of the preservative system.

Results are reported in the Table 2 below.

All the inventive examples presented below in Table 2 are similar to Inventive Example 1 described above. They only differ in the amount of sodium benzoate. The balance is done by adjusting the amount of water.

All the comparative examples presented below in Table 2 are similar to the inventive Example 1 described above. They only differ in the type of preservative used. In our case of Comparative Examples contain potassium sorbate as a preservative and at different concentrations. The balance is done by adjusting the amount of water.

TABLE 2

Stability Experiments

| Examples | Preservative | Concentration | Results (after 10 days at 60° C.) |
|---|---|---|---|
| Inventive Ex. 1 | Sodium Benzoate | 0.05% | Clear/colorless |
| Inventive Ex. 2 | Sodium Benzoate | 0.10% | Clear/colorless |
| Inventive Ex. 3 | Sodium Benzoate | 0.20% | Clear/colorless |
| Comparative Ex. 1 | Potassium Sorbate | 0.05% | Mostly colorless but lower clarity |
| Comparative Ex. 2 | Potassium Sorbate | 0.10% | Slightly yellow |
| Comparative Ex. 4 | Potassium Sorbate | 0.20% | Slightly yellow |
| Comparative Ex. 5 | None | N/A | Clear/colorless |
| Comparative Ex. 6* | Potassium Sorbate | 0.20% | Slightly yellow |

*contains no coco-betaine

The formulas were made as described above then placed at 60° C. for 10 days for accelerated stability. After 10 days, they were evaluated for color and clarity. It was observed that all the formulas containing sodium benzoate remained clear, while all the formulas containing potassium sorbate showed color/clarity issues. It was observed that the increased of the potassium sorbate concentrations made the formulas instable and turned yellow.

The presence of sodium benzoate to the formula contributes to the stabilization of the formula in terms of color and clarity.

While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed:

1. An aqueous micellar liquid composition consisting of:
   a) From 0.2% to 1.2% of an amphoteric surfactant selected from the group consisting of coco-betaine, lauryl betaine, oxyethylenated lauryl betaine, oxyethylenated stearyl betaine, cocamidopropyl betaine, lauramidopropyl betaine and mixtures thereof, by weight based on the total weight of the composition,
   b) From 0.06% to 0.9% of an alkyl polyglucoside by weight based on the total weight of the composition;
   c) at least 0.05% of sodium benzoate by weight based on the total weight of the composition;
   d) At least one or more water-soluble solvents selected from the group consisting of glycerin, C1-4 alcohols, organic solvents, polyols, glycols, and a mixture thereof;
   e) Phenylethyl alcohol;
   f) Citric acid; and
   g) Water.

2. The composition of claim 1, wherein the sodium benzoate stabilizes the aqueous micellar liquid composition.

3. The composition of claim 1, wherein the presence of sodium benzoate prevents the composition to become yellow.

4. The composition of claim 1, wherein the sodium benzoate is present in the amount up to 1% by weight based on the total weight of the composition.

5. The composition of claim 1, wherein the amphoteric surfactant is coco-betaine.

6. The composition of claim 1, wherein the amphoteric surfactant is present in the amount of from 0.3% to 1% by weight based on the total weight of the composition.

7. The composition of claim 1, wherein the alkyl polyglucoside is selected from the group consisting of lauryl glucoside, octyl glucoside, decyl glucoside, coco glucoside, caprylyl/capryl glucoside, and a mixture thereof.

8. The composition of claim 7, wherein the alkyl polyglucoside is caprylyl/capryl glucoside.

9. The composition of claim 1, wherein the alkyl polyglucoside is present in the amount of from 0.1% to 0.5% by weight based on the total weight of the composition.

10. The composition of claim 1, wherein the at least one or more water-soluble solvents is propanediol.

11. A method for removing makeup from keratinous fibers, said method comprising applying the composition of claim 1 to the keratinous fibers upon which makeup is applied, and removing at least a portion of the makeup from the keratinous fibers.

12. A method for cleansing skin comprising applying the composition of claim 1 to the skin and removing at least a portion of the composition from the skin.

13. An aqueous micellar liquid composition consisting of:
   a) From 0.2% to 1.2% of coco-betaine by weight based on the total weight of the composition;
   b) From 0.06% to 0.9% of caprylyl/capryl glucoside by weight based on the total weight of the composition;
   c) From 0.05% to 0.5% of sodium benzoate by weight based on the total weight of the composition;
   d) At least one or more water-soluble solvents selected from the group consisting of glycerin, C1-4 alcohols, organic solvents, polyols, glycols, and a mixture thereof;
   e) Phenylethyl alcohol;
   f) Citric acid; and
   g) Water.

* * * * *